(12) United States Patent
Omar et al.

(10) Patent No.: US 10,683,267 B1
(45) Date of Patent: Jun. 16, 2020

(54) ANTIDIABETIC COMPOUNDS (71) Applicant: King Abdulaziz University, Jeddah (SA)

(72) Inventors: Abdelsattar M. Omar, Jeddah (SA); Mohamed A. El-Zahabi, Cairo (EG); Salah G. Atteiah, Zagazig (EG); Ashraf B. Abdel-Naim, Jeddah (SA); Moustafa E. El-Araby, Jeddah (SA)

(73) Assignee: KING ABDULAZIZ UNIVERSITY, Jeddah (SA)

( * ) Notice: Subject to any disclaimer, the term of this patent is extended or adjusted under 35 U.S.C. 154(b) by 0 days.

(21) Appl. No.: 16/690,556

(22) Filed: Nov. 21, 2019

(51) Int. Cl.
| | |
|---|---|
| *C07C 13/18* | (2006.01) |
| *C07D 207/16* | (2006.01) |
| *A61P 3/10* | (2006.01) |
| *C07D 471/04* | (2006.01) |
| *C07D 209/52* | (2006.01) |

(52) U.S. Cl.
 CPC .............. *C07D 207/16* (2013.01); *A61P 3/10* (2018.01); *C07D 209/52* (2013.01); *C07D 471/04* (2013.01)

(58) Field of Classification Search
 CPC .................................................... C07C 13/18
 See application file for complete search history.

(56) References Cited

PUBLICATIONS

STN Reg No. 1002050-43-2, entered into STN on Feb. 7, 2008 (Year: 2008).*
STN Reg No. 1001980-72-8, entered into STN on Feb. 7, 2008 (Year: 2008).*
STN Reg No. 1001833-16-4, entered into STN on Feb. 7, 2008 (Year: 2008).*
CA Reg No. 1268996-28-6, entered Mar. 21, 2011 (Year: 2011).*

* cited by examiner

*Primary Examiner* — Karen Cheng
(74) *Attorney, Agent, or Firm* — W & C IP (57) ABSTRACT

Compounds for the treatment of hyperglycemia and/or diabetes are provided. The compounds, which inhibit the enzyme dipeptidyl peptidase (DPP-4), are based on the structure

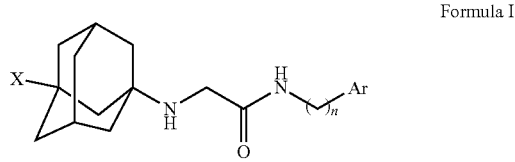

Formula I where X may be present or absent an may be OH, Ar is an aryl group; and n ranges from 0 to 5.

3 Claims, 2 Drawing Sheets

ANTIDIABETIC COMPOUNDS

BACKGROUND OF THE INVENTION

Field of the Invention

The invention generally relates to new compounds for the treatment of hyperglycemia and/or diabetes. In particular, the compounds inhibit the enzyme dipeptidyl peptidase (DPP-4), and are used to prevent or treat Type II diabetes.

Description of Related Art

The dominance of Type 2 Diabetes Mellitus (T2DM) is increasing worldwide, especially in South Asia. India is the country with the highest diabetes incidence. The number of people with diabetes in India will reach 80 million by the year 2025 according to the International Diabetes Federation (IDF).

At least seven different classes of agents are used as monotherapy, or in combinations, for the treatment of diabetes mellitus. These classes are represented by metformin, sulphonylureas, meglinitides, alpha-glucosidase inhibitors, thiazolidinediones (TZD), glucagon like peptide-1 (GLP-1) agonists and insulin. Unfortunately, many of these agents exhibit reduced efficacy over time, leading to insufficient glycemic control. Some of these agents are also associated with adverse effects that include weight gain, hypoglycemia and gastrointestinal distress. Therefore, alternative therapies are needed to overcome the limitations associated with conventional anti-hyperglycemic medications.

SUMMARY OF THE INVENTION

Figure 1:
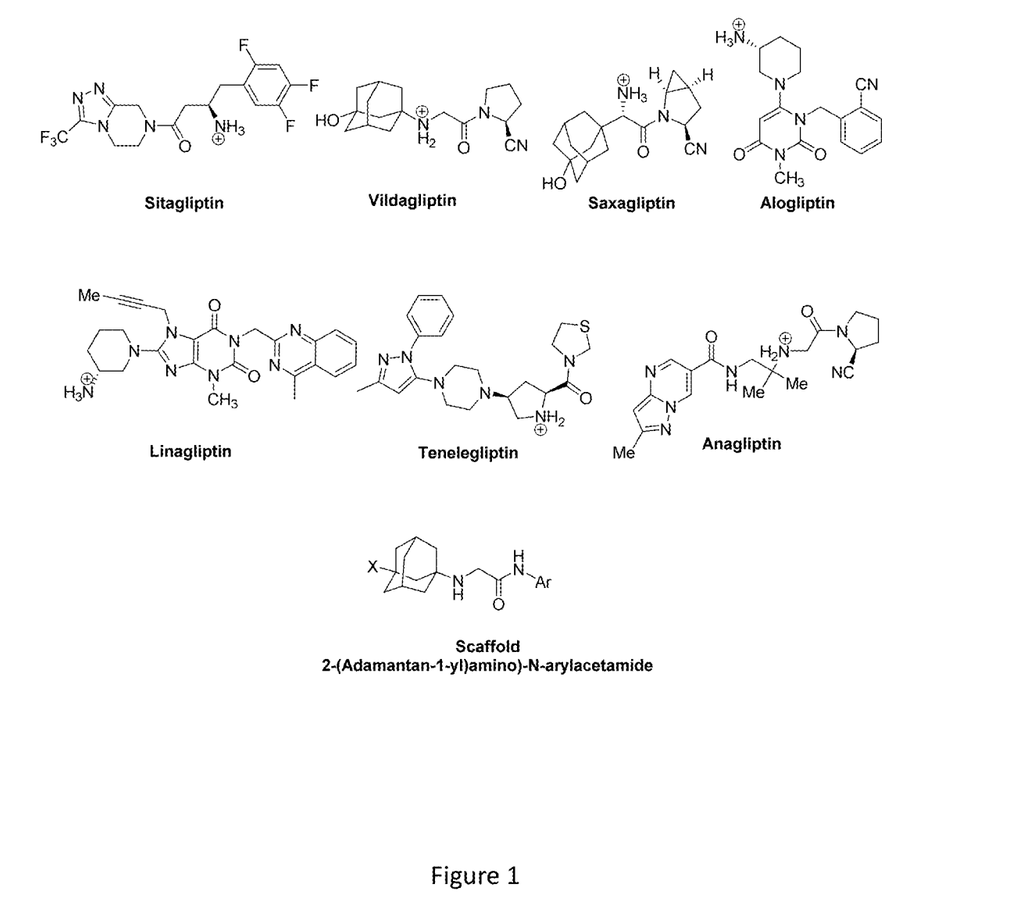
FIG. 1. Structural features of DPP-4 inhibitors and some examples of marketed drugs.

DPP-4 inhibitors are of intense interest in the development of a new diabetes therapy and several are currently marketed (FIG. 1). From a medicinal chemistry perspective, the DPP-4 inhibitor vildagliptin possesses a simple structure with no stereogenic centers, and can be prepared in only two simple steps of synthesis. However, being a pyrrolylnitrile derivative, it is prone to molecular instability due to the electrophilic nature of the nitrile group. It may undergo intramolecular cyclization by attack of the nucleophilic amino group of the sp-hybridized carbon of the nitrile group to form a ring of convenient size (6-membered piperazine ring). Therefore, the structure of vildagliptin was envisaged as surrogate for identifying novel DPP-4 inhibitors with high efficacy, increased stability and good safety profiles, for the design and development of drug candidates for treating and controlling T2DM.

Other features and advantages of the present invention will be set forth in the description of invention that follows, and in part will be apparent from the description or may be learned by practice of the invention. The invention will be realized and attained by the compositions and methods particularly pointed out in the written description and claims hereof.

It is an object of this invention to provide a compound of generic structure

Formula I where X may be present or absent and is OH, H; $CF_3$; $CHF_2$; $CH_2F$; CN; OR, NHR, NHCOR or $NHSO_2R$, where $R=(CH_2)nCH_3$, and n=0-2, or where R=cyclopropyl, cyclobutyl, oxetanyl, or oxolanyl; Ar is an aryl group; and n ranges from 0 to 5. In some aspects, X is absent or is OH. In other aspects, Ar is a 5-membered aromatic ring that is substituted or unsubstituted and optionally comprises one or more substituents. In some aspects, the 5-membered ring is an azole. In additional aspects, the azole is thiazole, isothiazole, imidazole, pyrazole, oxazole or isoxazole. In further aspects, the azole is thiazole. In additional aspects, the one or more substituents is a halogen. In yet further aspects, n=0 and the one or more substituents is Cl. In other aspects, Ar is a 6-membered aromatic ring that is substituted or unsubstituted and optionally comprises one or more substituents. In some aspects, the 6-membered aromatic ring is pyridine, X is absent and n=0. In other aspects, the one or more substituents is Cl. In additional aspects, the 6-membered aromatic ring is phenyl and n=0, 1 or 2. And in still further aspects, the one or more substituents is at least one of: a halogen; OH; a nitrogen containing group; a lower alkyl or halogenated alkyl; or an ester. In additional aspects, the one or more substituents is $CH_3$; OH; $CF_3$; $OCOCH_3$; CN; F; Cl; nitrile; or two $CH_3$ groups, each of which is attached to a different C atom of the phenyl, and n=0. In some aspects, X is absent and the one or more substituents is CN, OH, Cl, nitrile or two $CH_3$ groups, each of which is attached to a different C atom of the phenyl; or X is OH, n=0 and the one or more substituents is $CH_3$, OH, $CF_3$, $OCOCH_3$, CN, F, Cl; or X is OH, n=1 and the one or more substituents is F. In further aspects, X is OH, n=0, Ar is phenyl and the one or more substituents is CN; or X is absent, n=0 and Ar is pyridine.

5. The compound of claim 4, wherein azole is thiazole, isothiazole, imidazole, pyrazole, oxazole or isoxazole.

6. The compound of claim 4, wherein the 5-membered aromatic ring is thiazole.

7. The compound of claim 4, wherein n=0 and the one or more substituents is a halogen.

The invention also provides a method of preventing or treating hyperglycemia in a subject in need thereof, comprising administering to the subject a therapeutically effective amount of a compound of generic structure Formula I where X may be present or absent and is OH; Ar is an aryl group; and n ranges from 0 to 5. In some aspects, X is absent or is OH. In some aspects, the subject has Type II diabetes.

The invention also provides a method of inhibiting dipeptidyl peptidase (DPP-4), comprising contacting the DPP-4 with a compound of generic structure Formula I where X may be present or absent and is OH; Ar is an aryl group; and n ranges from 0 to 5.

DETAILED DESCRIPTION

Figure 2:
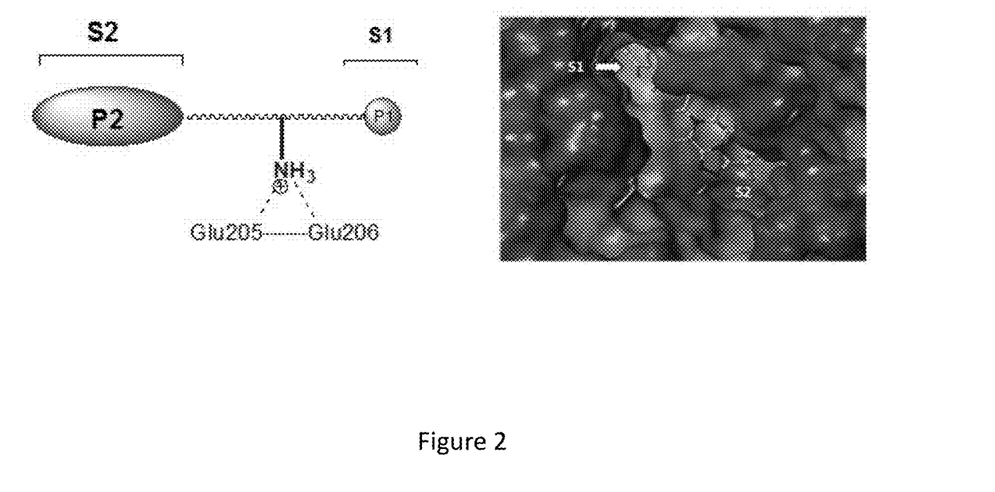
FIG. 2. Active site of DPP-4 in crystal structure of complex with sitagliptin (PDB code: 1X70).

From a molecular design point of view, the binding potency of vildagliptin and other first generation inhibitors depends on satisfying the distinctive features of the S1 and S2 pockets of DPP-4. The S1 pocket is a small hydrophobic cleft surrounded by very hydrophobic environment composed of Tyr-547, Trp-659, Tyr-662, Tyr-666, Val-711 and other residues. The OH of Ser-630 also intrudes into this pocket and is a member of the catalytic triad of residues that attack the scissile electrophilic carbonyl of the substrate peptides (FIG. 2). The S2 pocket has two main features: two glutamic acids in the bridge area between the S1 and S2 and a large hydrophobic pocket that is lined by Phe-357 and Arg-358. Glu-205/Glu-206 were found to bind with a basic nitrogen, which is present in all designed DPP-4 inhibitors to date. The S2 hydrophobic extension can accommodate bulky hydrophobic groups such as adamantane in vildagliptin and sitagliptin since bulkiness secures good selectivity. The P2 groups are well represented by a wide variety sub-structures including aliphatics, biaryls, heterocyclics, etc. The presence of a bulky group at this position insures binding selectivity towards DPP-4 over other dipeptidyl peptidases (e.g. DPP2, DPP8 and DPP9).

The approach taken herein to discover new DPP-4 inhibitors depended on conserving the adamantylamine group attached to glycine as a P2 group and changing the pyrrolylnitrile to variety of aromatic and heteroaromatic groups with small substituents. In general, the substituents included hydrophobic, hydrophilic, electron-donating and electron-withdrawing groups. In addition, some alicyclic groups were used to complete the SAR coverage of P1 position. Different ortho, meta and para substituents with different electronic properties were also assessed. However, the size these substituents was limited in order to lessen the potential negative impact of large groups on the binding with DPP-4.

The DPP-4 inhibitors described herein have a generic structure as depicted as "scaffold" in FIG. 1 and in Formula I:

Formula I where X may be present or absent and if present is selected from the group consisting of OH; H; $CF_3$; $CHF_2$; $CH_2F$; CN; OR, NHR, NHCOR, $NHSO_2R$, where $R=(CH_2)nCH_3$, and n=0-2, or where R=cyclopropyl, cyclobutyl, oxetanyl, or oxolanyl;
Ar is an aryl group; and
n ranges from 0 to 5.

Aryl refers to any organic group derived from an aromatic hydrocarbon by the removal of a hydrogen atom. Examples of suitable aryl groups include but are not limited to: monocyclic substituted and unsubstituted 5- and 6-membered aromatic rings, which may also include one or more substituents attached to the ring. As used herein, a "substituted" ring refers to a ring in which a carbon atom is replaced by a heteroatom (a non-carbon atom) in the ring. A "substituent" refers to a chemical group (i.e. a functional group) that is attached to at least one atom of the ring.

Exemplary 5-membered aryl rings include rings such as pyrrole and various substituted heterocyclic pyrrole rings. Heteroatoms that may be independently selected and substituted for a C atom of the ring include but are not limited to one or more of: O, S, N, etc. One or more than one of the same heteroatom may be present. In some aspects, the 5-membered heterocyclic ring is an azole, such as thiazole, isothiazole, imidazole, pyrazole, oxazole, isoxazole, etc.

The 5-membered aryl ring may have one or more independently selected substituents attached to the ring. One or more than one of the same substituent may be present. Examples of substituents include but are not limited to: halogen (such as Cl, Br, F, etc.); OH; $CF_3$; $CHF_2$; $CH_2F$; CN; or R, OR, NHR, NHCOR, or $NHSO_2R$, where $R=(CH_2)nCH_3$ and n=0-2, or R=cyclopropyl, cyclobutyl, oxetanyl, oxolanyl.

In some aspects, the 5-membered aryl ring is thiazole (two heteroatoms, S and N); and in other aspects the 5-membered aryl ring is thiazole with a Cl substituent.

Exemplary 6-membered aryl rings include rings such as phenyl and various substituted heterocyclic phenyl rings, including ortho, meta and para isomers thereof. Heteroatoms that may be independently selected include but are not limited to one or more of: O, S, N, etc. One or more than one of the same heteroatom may be present. In some aspects, the 6-membered aryl ring is a phenyl ring and in other aspects it is a pyridine ring (one N heteroatom).

The 6-membered aryl ring may have one or more independently selected substituents attached to the ring. One or more than one of the same substituent may be present. Examples of substituents include but are not limited to: halogen (such as Cl, Br, F, etc.); OH; a nitrogen containing group (such as CN; nitrile; OR, NHR, NHCOR, $NHSO_2R$, where $R=(CH_2)nCH_3$ and n=0-2, or R=cyclopropyl, cyclobutyl, 2-oxo-5-oxetanyl, 2-oxo-5-oxolanyl, etc.); a lower alkyl such as methyl, ethyl, propyl, etc. and halogenated alkyls such as $CF_3$; and esters OCOR where R=lower alkyl such as methyl, ethyl propyl, cyclopropyl, etc.

In some aspects, the 6-membered aryl ring is phenyl, or phenyl with a substituent that is OH, Cl, F, $CF_3$, $OCOCH_3$, nitrile, CN, $CH_3$, or two $CH_3$ groups each of which is attached to a different C atom of the ring. In other aspects, the 6-membered aryl ring is pyridine, or pyridine with a substituent that is Cl.

Enantiomers, mixtures of enantiomers, diastereomers, tautomers, racemates and other isomers, such as rotamers, and pharmaceutically acceptable salts of each of the compounds are also encompassed.

In some aspects, X is absent or is OH.

In some aspects, Ar is a 5-membered aromatic ring that is substituted or unsubstituted and optionally comprises one or more substituents. For example, the 5-membered aromatic ring can be thiazole, with or without a halogen substituent such as Cl.

Alternatively, Ar is a 6-membered aromatic ring that is substituted or unsubstituted and optionally comprises one or more substituents. For example, the 6-membered aromatic ring can be pyridine, with or without a halogen substituent such as Cl. In some such cases, X is absent and n=0.

In still further alternatives, the 6-membered aromatic ring is phenyl and n=0, 1 or 2. When the 6-membered aromatic ring is phenyl, the one or more substituents (which may be present or absent), if present, are for example, at least one of OH; a nitrogen containing group; a lower alkyl or halogenated alkyl; or an ester. In particular, the one or more substituents can be $CH_3$; OH; $CF_3$; $OCOCH_3$; CN; F; Cl; nitrile; or two $CH_3$ groups, each of which is attached to a different C atom of the phenyl, and n=0.

Further examples of the phenyl containing compounds include: those in which X is absent and the one or more substituents is CN, OH, Cl, nitrile or two $CH_3$ groups, each of which is attached to a different C atom of the phenyl; those in which X is OH, n=0 and the one or more substituents is $CH_3$, OH, $CF_3$, $OCOCH_3$, CN, F, Cl; and those in which X is OH, n=1 and the one or more substituents is F.

Exemplary compounds disclosed herein include but are not limited those depicted below, where numbering of compounds is the same as that used in the biological data graphs presented herein.

GLP-1

GLP-2

GLP-3

GLP-4

GLP-5

GLP-14

GLP-15

GLP-16

GLP-17

GLP-19

GLP-26

GLP-27

GLP-30

GLP-31

GLP-53

GLP-43

GLP-54

GLP-59

GLP-60

GLP-73

GLP-107

GLP-110

GLP-111

GLP-112

GLP-117

GLP-118

GLP-119

GLP-120

Compositions and Administration

The compounds described herein are generally delivered (administered) as a pharmaceutical composition. Such pharmaceutical compositions generally comprise at least one of the disclosed compounds, i.e. one or more than one (a plurality) of different compounds (e.g. 2 or more such as 2, 3, 4, 5, 6, 7, 8, 9, 10 or more) may be included in a single formulation. Accordingly, the present invention encompasses such formulations and compositions. The compositions generally include one or more substantially purified compounds as described herein, and a pharmacologically suitable (physiologically compatible) carrier, which may be aqueous or oil-based. In some aspects, such compositions are prepared as liquid solutions or suspensions, or as solid forms such as tablets, pills, powders and the like. Solid forms suitable for solution in, or suspension in, liquids prior to administration are also contemplated (e.g. lyophilized forms of the compounds), as are emulsified preparations. In some aspects, the liquid formulations are aqueous or oil-based suspensions or solutions. In some aspects, the active ingredients are mixed with excipients which are pharmaceutically acceptable and compatible with the active ingredients, e.g. pharmaceutically acceptable salts. Suitable excipients include, for example, water, saline, dextrose, glycerol, ethanol and the like, or combinations thereof. In addition, the composition may contain minor amounts of auxiliary substances such as wetting or emulsifying agents, pH buffering agents, preservatives, and the like. If it is desired to administer an oral form of the composition, various thickeners, flavorings, diluents, emulsifiers, dispersing aids or binders and the like are added. The composition of the present invention may contain any such additional ingredients so as to provide the composition in a form suitable for administration. The final amount of compound in the formulations varies, but generally from about 1-99%. Still other suitable formulations for use in the present invention are found, for example in Remington's Pharmaceutical Sciences, 22nd ed. (2012; eds. Allen, Adejarem Desselle and Felton).

Some examples of materials which can serve as pharmaceutically acceptable carriers include, but are not limited to: ion exchangers, alumina, aluminum stearate, lecithin, serum proteins (such as human serum albumin), buffer substances (such as Tween® 80, phosphates, glycine, sorbic acid, or potassium sorbate), partial glyceride mixtures of saturated vegetable fatty acids, water, salts or electrolytes (such as protamine sulfate, disodium hydrogen phosphate, potassium hydrogen phosphate, sodium chloride, or zinc salts), colloidal silica, magnesium trisilicate, polyvinyl pyrrolidone, polyacrylates, waxes, polyethylene-polyoxypropylene-block polymers, methylcellulose, hydroxypropyl methylcellulose, wool fat, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol or polyethylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

"Pharmaceutically acceptable salts" refers to the relatively non-toxic, inorganic and organic acid addition salts, and base addition salts, of compounds of the present invention. These: salts can be prepared in situ during the final isolation and purification of the compounds. In particular, acid addition salts can be prepared by separately reacting the purified compound in its free base form with a suitable organic or inorganic acid and isolating the salt thus formed. Exemplary acid addition salts include the hydrobromide, hydrochloride, sulfate, bisulfate, phosphate, nitrate, acetate, oxalate, valerate, oleate, palmitate, stearate, laurate, borate, benzoate, lactate, phosphate, tosylate, citrate, maleate, fumarate, succinate, tartrate, naphthylate, mesylate, glucoheptonate, lactiobionate, sulfamates, malonates, salicylates, propionates, methylene-bis-.beta.-hydroxynaphthoates, gentisates, isethionates, di-p-toluoyltartrates, methanesulfonates, ethanesulfonates, benzenesulfonates, p-toluenesulfonates, cyclohexylsulfamates and laurylsulfonate salts, and the like. See, for example S. M. Berge, et al., "Pharmaceutical Salts," J. Pharm. Sci., 66, 1-19 (1977) which is incorporated herein by reference. Base addition salts can also be prepared by separately reacting the purified compound in its acid form with a suitable organic or inorganic base and isolating the salt thus formed. Base addition salts include pharmaceutically acceptable metal and amine salts. Suitable metal salts include the sodium, potassium, calcium, barium, zinc, magnesium, and aluminum salts. The sodium and potassium salts are preferred. Suitable inorganic base addition salts are prepared from metal bases which include sodium hydride, sodium hydroxide, potassium hydroxide, calcium hydroxide, aluminum hydroxide, lithium hydroxide, magnesium hydroxide, zinc hydroxide and the like. Suitable amine base addition salts are prepared from amines which have sufficient basicity to form a stable salt, and preferably include those amines which are frequently used in medicinal chemistry because of their low toxicity and acceptability for medical use. ammonia, ethylenediamine, N-methyl-glucamine, lysine, arginine, ornithine, choline, N,N'-dibenzylethylenediamine, chloroprocaine, diethanolamine, procaine, N-benzylphenethylamine, diethylamine, piperazine, tris(hydroxymethyl)-aminomethane, tetramethylammonium hydroxide, triethylamine, dibenzylamine, ephenamine, dehydroabietylamine, N-ethylpiperidine, benzylamine, tetramethylammonium, tetraethylammonium, methylamine, dimethylamine, trimethylamine, ethylamine, basic amino acids, e.g., lysine and arginine, and dicyclohexylamine, and the like.

The compounds may be administered in vivo by any suitable route including but not limited to: by injection (e.g. intravenous, intraperitoneal, intramuscular, subcutaneous, and the like), by absorption through epithelial or mucocutaneous linings (e.g., nasal, oral, gastrointestinal mucosa, and the like); or, orally (e.g. as a pill, capsule, liquid, etc.). In preferred embodiments, the mode of administration is oral.

In addition, the compositions may be administered in conjunction with other treatment modalities such as other drugs used to treat hyperglycemia and/or diabetes, e.g. a sulphonylurea, a thiazolidinedione, metformin, and/or insulin. The compositions may be administered with a separate composition of one or more other drugs (especially for insulin, which is typically injected); or the one or more other drugs may be combined together with one or more of the present compounds in a single preparation, e.g. in a tablet that includes a compound as described herein and one or more of e.g. a sulphonylurea, a thiazolidinedione and metformin.

Methods of Treatment

The invention also encompasses methods of using the compounds to treat hyperglycemia (high blood sugar, high blood glucose) and diseases and conditions associated with high blood sugar, such as pre-diabetes, diabetes, hyperosmolar hyperglycemic nonketotic syndrome (HHNS), etc. "Hyperglycemia" may refer to fasting hyperglycemia, defined as a blood glucose level above 130 mg/dL after at least 8 hours of fasting; and/or postprandial or reactive hyperglycemia defined as a blood glucose level above 180 mg/dL 1-2 hours after eating. The type of diabetes that is treated may be Type I or Type II, and is usually Type II. The treatment methods include a step of administering to a subject in need thereof a therapeutically effective amount of at least one compound disclosed herein. Administration of the compounds is therapeutically effective to treat or prevent at least one symptom of hyperglycemia and related or associated diseases, such as but not limited to: frequent urination, increased thirst, blurred vision, fatigue, headache; the buildup of toxic acids (ketones) in blood and urine (ketoacidosis), signs and symptoms of which include: fruity-smelling breath, nausea and vomiting, shortness of breath, dry mouth, weakness, confusion, coma, and abdominal pain.

In some aspects, administration of the compounds completely prevents or reverses one or more symptoms of hyperglycemia and related or associated diseases and conditions. However, those of skill in the art will recognize that much benefit can accrue to a subject even if a complete cure or control of a disease or symptoms thereof does not take place Lowering or lessening, or decreasing the frequency of, or slowing the onset of one of more symptoms may also be of great benefit.

The amount of a compound of the invention may vary from subject to subject and from time period to time period for a given subject, depending on e.g. the weight, age, genetic background, overall health, etc. as well as the tendency of the subject to adopt life-style changes such as undertaking exercise and/or adopting healthy eating programs, which may decrease or eliminate the need for medication. Alternatively, a subject may develop a need for a higher dose over time, or may require a lower dose when the compound is administered with another anti-hypergylcemia drug. Generally, a single dose of a compound is in the range of from about 20 to about 500 mg per day, (e.g. about 20, 30, 40, 50, 60, 70, 80, 90, 100, 150, 200, 250, 300, 350, 400, 450 or 500 mg per dose), and preferably is about 50 mg per dose, taken once or twice a day, so that a total dose per day could be e.g. 50 (one per day) or 100 mg (50 mg twice per day). Alternatively, the compounds may be administered on the basis of mg/kg of body weight, such as about 50 mg/kg (e.g. ranging from about 1 to 500 mg/kg, such as about 5, 10, 20, 25, 30, 35, 40, 45, 50, 55, 60, 65, 70, 75, 80, 85, 90, 95, 100, 125, 150, 175, 200, 225, 250, 275, 300, 325, 350, 375, 400, 425, 450, or 500 mg/kg.

It is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Representative illustrative methods and materials are herein described; methods and materials similar or equivalent to those described herein can also be used in the practice or testing of the present invention.

All publications and patents cited in this specification are herein incorporated by reference as if each individual publication or patent were specifically and individually indicated to be incorporated by reference, and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual dates of public availability and may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as support for the recitation in the claims of such exclusive terminology as "solely," "only" and the like in connection with the recitation of claim elements, or use of a "negative"

limitations, such as "wherein [a particular feature or element] is absent", or "except for [a particular feature or element]", or "wherein [a particular feature or element] is not present (included, etc.) . . . ".

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

The invention is further described by the following non-limiting examples which further illustrate the invention, and are not intended, nor should they be interpreted to, limit the scope of the invention.

Example

Type 2 Diabetes Mellitus (T2DM) is wide-spread non-infectious chronic illness that can be controlled by increasing endogenous substances called gliptins. Gliptins are destroyed by the enzyme dipeptidyl peptidase (DPP-4), a serine protease that excises the first two terminal amino acids of gliptins. This Example describes the utilization of some structural features of vildagliptin, saxagliptin and sitagliptin, well known antidiabetic drugs which are DPP-4 inhibitors, to design novel compounds that possess antidiabetic activity in animal models of induced high glucose levels and with induced diabetes. Selected compounds demonstrated strong inhibition of DPP-4, the major target of gliptin antidiabetic agents.

Materials and Methods

A. Chemical Synthesis

Chemicals used in the syntheses were Aldrich, Sigma and/or Fluka products and were used without further purification.

The compounds were synthesized according to Scheme 1. The reactions were monitored by TLC using Merck pre-coated silica gel 60F 254 plates.

Scheme 1

GLP-1 to GLP-122

Characterization of Compounds

All compounds were confirmed with techniques such as $^1$H NMR, $^{13}$C NMR, FT-IR and LC/MS.

Nuclear magnetic resonance ($^1$HNMR) spectra were obtained on 600 MHz Bruker Advance DPX600 spectrometer at Faculty of Science, King Abdulaziz University using Me$_4$Si as the internal reference, and DMSO-d$_6$ or CDCl$_3$ were used as solvents. The chemical shifts were measured in δ ppm. General procedure for the synthesis of target compounds.

To a solution of arylamines (10 mmol) in DCM, triethylamine (1.1 eq.) was added. The solution was cooled to (0° C.) and chloroacetyl chloride (1 eq.) was added in a drop-wise manner over a period of 20 minutes. After completion of chloracetyl chloride addition, the reaction mixture was stirred at room temperature for 4 hours. The reaction mixture was extracted with dilute HCl, brine and dried over anhydrous MgSO$_4$. The mixture was filtered off and the filtrate was evaporated under vacuum.

The intermediate N-aryl-2-chloracetamides (1 mmol) were mixed with 10 ml of Isopropyl acetate, the mixture was mildly heated until the substance was dissolved. Before further use, the solution was mixed with 40 ml of 2-butanone, potassium iodide (0.05 equivalent) and potassium carbonate (4 mmol) were added to the stirred suspension. The suspension was stirred in a bath with the temperature of 35-40° C. and the solution prepared in accordance was added dropwise during 1.25 h. then, the reaction mixture was stirred at 37° C. for 1 h and thereafter it was heated to moderate reflux (75-80° C.) for 30 m. Subsequently, the hot suspension was filtered, the filtration cake was washed with 3×50 ml hot 2-butanone. The obtained clear filtrate was stirred under slow cooling, during which the solution became cloudy due to separation of the product. The suspension was stirred at laboratory temperature. Then filtration followed and the cake was washed with 2×100 ml of Isopropyl acetate. A white crystalline powder was obtained with high purity.

Melting points were determined with a Barnested electrothermal melting point apparatus and are uncorrected. The chemicals, reagents and solvents were purchased from Aldrich chemical company and other international companies through Bayouni trading companies in Saudi Arabia.

NMR Data of GLP Compounds

N.B. All compounds were confirmed with LC/MS and showed excellent purities (over 95%) $^1$H NMR of GLP-1: DMSO-d$_6$, δ 1.43 (brs, 2H, CH$_2$), 1.46 (brs, 6H, 2CH$_2$, 2 CH), 1.50-1.51 (brs, 4H, 2CH$_2$), 2.13 (brs, 2H, CH$_2$), 2.33 (br, 1H, NH—CH$_2$), 3.24 (brs, 2H, CH$_2$), 4.45 (brs, 1H, OH), 7.04-7.07 (t, 1H, Arom-H), 7.29-7.33 (t, 2H, Arom-H) 7.60-7.63 (d, 2H, Arom-H), 9.88 (brs, 1H, NH).

$^1$H NMR of GLP-2: DMSO-d$_6$, δ 1.43 (brs, 2H, CH$_2$), 1.48 (brs, 6H, 2CH$_2$, 2 CH), 1.51 (brs, 4H, 2CH$_2$), 2.14 (brs, 2H, CH$_2$), 2.26 (s, 3H, CH$_3$), 2.75 (br, 1H, NH—CH$_2$), 3.23 (brs, 2H, CH$_2$), 4.46 (brs, 1H, OH), 6.99-7.03 (t, 1H, Arom-H), 7.16-7.18 (d, 1H, Arom-H) 7.20-7.23 (t, 1H, Arom-H), 8.01-8.03 (d, 1H, Arom-H), 9.86 (brs, 1H, NH).

$^1$H NMR of GLP-3: DMSO-d$_6$, δ 1.43 (brs, 2H, CH$_2$), 1.46-1.47 (brs, 6H, 2CH$_2$+2 CH), 1.51-1.51 (brs, 4H, 2CH$_2$), 2.13 (brs, 2H, CH$_2$), 2.25 (s, 3H, CH$_3$), 2.30 (br, 1H, NH—CH$_2$), 3.22 (brs, 2H, CH$_2$), 4.41 (brs, 1H, OH), 7.10-7.12 (d, 2H, Arom-H), 7.49-7.51 (d, 2H, Arom-H), 9.74 (brs, 1H, NH).

$^1$H NMR of GLP-5: DMSO-d$_6$, δ 1.42 (brs, 2H, CH$_2$), 1.46 (brs, 6H, 2CH$_2$, 2 CH), 1.50 (brs, 4H, 2CH$_2$), 2.13 (brs, 2H, CH$_2$), 2.78 (br, t, 1H, NH—CH$_2$), 3.33 (brs, 2H, CH$_2$), 3.88 (s, 3H, OCH$_3$), 4.45 (brs, 1H, OH), 6.90-6.93 (m, 1H, Arom-H), 7.00-7.07 (m, 1H, Arom-H) 8.24-8.25 (d, 1H, Arom-H), 10.27 (brs, 1H, NH).

$^1$H NMR of GLP-14: DMSO-$d_6$, δ 1.44 (brs, 2H, CH$_2$), 1.48 (brs, 6H, 2CH$_2$, 2 CH), 1.52 (brs, 4H, 2CH$_2$), 2.16 (brs, 2H, CH$_2$), 2.56 (br, 1H, NH—CH$_2$), 3.27 (brs, 2H, CH$_2$), 4.54 (brs, 1H, OH), 7.31-7.33 (t, 1H, Arom-H), 7.70-7.72 (t, 1H, Arom-H) 7.75-7.76 (d, 1H, Arom-H), 8.51-8.53 (d, 1H, Arom-H), 10.5 (brs, 1H, NH).

$^1$H NMR of GLP-15: DMSO-$d_6$, δ 1.45 (brs, 2H, CH$_2$), 1.49 (brs, 6H, 2CH$_2$, 2 CH), 1.53 (brs, 4H, 2CH$_2$), 2.16 (brs, 2H, CH$_2$), 2.57 (br, 1H, NH—CH$_2$), 3.31 (brs, 2H, CH$_2$), 4.51 (brs, 1H, OH), 7.44-7.45 (d, 1H, Arom-H), 7.59-7.61 (t, 1H, Arom-H) 7.89-7.91 (d, 1H, Arom-H), 8.20 (s, 1H, Arom-H), 10.2 (brs, 1H, NH).

$^1$H NMR of GLP-16: DMSO-$d_6$, δ 1.44 (brs, 2H, CH$_2$), 1.51 (brs, 6H, 2CH$_2$, 2 CH), 1.54 (brs, 4H, 2CH$_2$), 2.15 (brs, 2H, CH$_2$), 2.69-2.71 (br, 1H, NH—CH$_2$), 3.28 (brs, 2H, CH$_2$), 3.45 (s, 3H, OCH$_3$), 4.50 (brs, 1H, OH), 7.18-7.21 (d, 1H, Arom-H), 7.63-7.65 (t, 1H, Arom-H) 7.99-8.01 (d, 1H, Arom-H), 8.58-8.59 (d, 1H, Arom-H), 12.11 (brs, 1H, NH).

$^1$H NMR of GLP-17: DMSO-$d_6$, δ 1.45 (brs, 2H, CH$_2$), 1.48 (brs, 6H, 2CH$_2$, 2 CH), 1.53 (brs, 4H, 2CH$_2$), 2.15 (brs, 2H, CH$_2$), 2.36 (br, 1H, NH—CH$_2$), 3.24 (brs, 2H, CH$_2$), 4.51 (brs, 1H, OH), 6.47-6.50 (dd, 1H, Arom-H), 6.96-6.97 (d, 1H, Arom-H) 7.09-7.12 (d, 1H, Arom-H), 7.25 (s, 1H, Arom-H), 9.46 (brs, 1H, OH), 9.76 (s, 1H, NH).

$^1$H NMR of GLP-19: CDCl$_3$, δ 1.52-1.53 (br, t, 2H, CH$_2$), 1.62-1.63 (br, d, 6H, 2CH$_2$, 2 CH), 1.67 (brs, 4H, 2CH$_2$), 1.74 (brs, 1H, NH—CH$_2$), 2.29 (brs, 2H, CH$_2$), 3.42 (brs, 2H, CH$_2$), 4.62 (brs, 1H, OH), 7.13-7.16 (m, 1H, Arom-H), 7.57-7.60 (m, 2H, Arom-H) 8.54-8.56 (br, d, 1H, Arom-H), 10.64 (brs, 1H, NH).

$^1$H NMR of GLP-26: DMSO-$d_6$, δ 1.43 (brs, 2H, CH$_2$), 1.48 (brs, 6H, 2CH$_2$, 2 CH), 1.50 (brs, 4H, 2CH$_2$), 2.13 (brs, 2H, CH$_2$), 2.62 (br, 1H, NH—CH$_2$), 3.30 (brs, 2H, CH$_2$), 4.49 (brs, 1H, OH), 7.54-7.55 (m, 1H, Arom-H), 7.94-7.96 (dt, 1H, Arom-H) 8.17-8.18 (br, 1H, Arom-H), 10.18 (brs, 1H, NH).

$^1$H NMR of GLP-27: DMSO-$d_6$, δ 1.43 (brs, 2H, CH$_2$), 1.45-1.46 (br, d, 6H, 2CH$_2$, 2 CH), 1.50 (brs, 4H, 2CH$_2$), 2.14 (brs, 2H, CH$_2$), 2.62-2.63 (br, t, 1H, NH—CH$_2$), 3.26 (brs, 2H, CH$_2$), 4.50 (brs, 1H, OH), 7.10-7.14 (m, 1H, Arom-H), 7.18-7.20 (t, 1H, Arom-H) 7.29-7.32 (m, 1H, Arom-H), 8.20-8.22 (t, 1H, Arom-H), 10.09 (brs, 1H, NH).

$^1$H NMR of GLP-30: DMSO-$d_6$, δ 1.46 (brs, 2H, CH$_2$), 1.52 (brs, 6H, 2CH$_2$, 2 CH), 1.53 (brs, 4H, 2CH$_2$), 2.17 (brs, 2H, CH$_2$), 2.31 (s, 3H, CH$_3$), 2.75 (br, 1H, NH—CH$_2$), 3.23 (brs, 2H, CH$_2$), 4.55 (brs, 1H, OH), 6.99-7.03 (t, 1H, Arom-H), 7.16-7.18 (d, 1H, Arom-H), 7.20-7.23 (t, 1H, Arom-H), 8.01-8.03 (d, 1H, Arom-H), 9.86 (brs, 1H, NH).

$^1$H NMR of GLP-31: DMSO-$d_6$, δ 1.43 (brs, 2H, CH$_2$), 1.46-1.47 (br, d, 6H, 2CH$_2$, 2 CH), 1.50-1.51 (br, d, 4H, 2CH$_2$), 2.13 (brs, 2H, CH$_2$), 2.62-2.63 (br, t, 1H, NH—CH$_2$), 3.26 (brs, 2H, CH$_2$), 4.51 (brs, 1H, OH), 6.88-6.91 (m, 1H, Arom-H), 7.33-7.39 (m, 2H, Arom-H) 7.66-7.67 (m, 1H, Arom-H), 10.05 (brs, 1H, NH).

$^1$H NMR of GLP-43: CDCl$_3$, δ 1.49 (brs, 2H, CH$_2$), 1.55 (brs, 6H, 2CH$_2$, 2 CH), 1.60 (brs, 4H, 2CH$_2$), 2.22 (br, 1H, NH—CH$_2$), 2.28 (brs, 2H, CH$_2$), 3.36 (brs, 2H, CH$_2$), 4.81 (brs, 1H, OH), 7.28-7.29 (d, 2H, Arom-H), 7.53-7.54 (d, 2H, Arom-H) 10.53 (brs, 1H, NH).

$^1$H NMR of GLP-53: CDCl$_3$, δ 1.52 (br, t, 2H, CH$_2$), 1.62-1.63 (br, d, 6H, 2CH$_2$, 2 CH), 1.66 (brs, 4H, 2CH$_2$), 2.23 (brs, 1H, NH—CH$_2$), 2.27 (brs, 2H, CH$_2$), 3.43 (brs, 2H, CH$_2$), 4.42-4.46 (d, 2H, N—CH$_2$-Ph), 7.26-7.29 (m, 3H, Arom-H), 7.32-7.35 (m, 2H, Arom-H) 7.79 (br, t, 1H, —CO—NH—CH$_2$).

$^1$H NMR of GLP-54: CDCl$_3$, δ 1.49 (br, t, 2H, CH$_2$), 1.54 (br, d, 6H, 2CH$_2$, 2 CH), 1.67 (brs, 4H, 2CH$_2$), 2.23 (brs, 1H, NH—CH$_2$), 2.27 (brs, 2H, CH$_2$), 3.41 (brs, 2H, CH$_2$), 4.42-4.46 (d, 2H, N—CH$_2$-Ph), 7.00-7.03 (d, 2H, Arom-H), 7.25-7.27 (d, 2H, Arom-H) 7.74 (br, t, 1H, —CO—NH—CH$_2$).

$^1$H NMR of GLP-59: CDCl$_3$, δ 1.37 (brs, 2H, CH$_2$), 1.43 (br, 3H, CH+CH$_2$) 1.47-1.50 (br, m, 1H, CH$_2$), 1.56-1.58 (br, m, 2H, CH$_2$), 1.62-1.64 (br, m, 2H, CH$_2$), 2.03 (brs, 1H, NH—CH$_2$), 2.21 (brs, 2H, CH$_2$), 2.83-2.85 (t, 2H, CH$_2$-Ph), 3.2 (d, 2H, N—CH$_2$—CH$_2$), 3.53-3.56, (q, 2H, N—CH$_2$—CH$_2$), 7.21-7.25 (m, 3H, Arom-H), 7.30-7.33 (m, 2H, Arom-H), 7.59 (br, t, 1H, CO—NH).

$^1$H NMR of GLP-60: CDCl$_3$, δ 1.45 (brs, 2H, CH$_2$), 1.49 (brs, 6H, 2CH$_2$, 2 CH), 1.56 (brs, 4H, 2CH$_2$), 2.05 (brs, 2H, CH$_2$), 2.29 (br, 1H, NH—CH$_2$), 3.35 (s, 2H, CH$_2$), 4.58 (brs, 1H, OH), 6.80-6.83 (m, 2H, Arom-H), 7.40-7.43 (d, 2H, Arom-H), 9.34 (brs, 1H, OH), 9.44 (s, 1H, NH).

$^1$H NMR of GLP-73: DMSO-$d_6$, δ 0.85-0.88 (t, 1H, NH—CH$_2$), 1.25 (brs, 1H, CH$_2$), 1.42 (brs, 2H, CH$_2$), 1.48 (brs, 9H, 4CH$_2$+CH), 2.14 (brs, 2H, CH$_2$), 3.4 (brs, 1H, OH), 3.44 (s, 2H, CH$_2$), 7.46 (s, 1H, Arom-H).

$^1$H NMR of GLP-107: DMSO-$d_6$, δ 1.43 (brs, 2H, CH$_2$), 1.47 (brs, 6H, 2CH$_2$, 2 CH), 1.52 (brs, 4H, 2CH$_2$), 2.13 (brs, 2H, CH$_2$), 2.34 (br, 1H, NH—CH$_2$), 3.22 (brs, 2H, CH$_2$), 4.50 (brs, 1H, OH), 6.46-6.49 (dd, 1H, Arom-H), 6.94-6.95 (d, 1H, Arom-H) 7.07-7.10 (d, 1H, Arom-H), 7.24 (s, 1H, Arom-H), 9.43 (brs, 1H, OH), 9.72 (s, 1H, NH).

$^1$H NMR of GLP-110: DMSO-$d_6$, δ 1.57-1.59 (br, d, 3H, 3CH), 1.66-1.68 (br, d, 3H, 3CH), 1.90 (brs, 6H, 3CH$_2$), 2.13 (br, 1H, 3CH), 4.02-4.04 (t, 2H, CH$_2$), 7.59-7.60 (m, 2H, Arom-H), 7.92-7.94 (m, 1H, Arom-H), 8.12-8.13 (d, 1H, Arom-H) 9.11 (br, s, 1H, NH), 11.62 (s, 1H, NH).

$^1$H NMR of GLP-111: DMSO-$d_6$, δ 1.56-1.57 (br, m, 9H, 3CH$_2$), 1.61-1.63 (br, m, 2H, CH$_2$), 2.01 (brs, 4H, CH$_2$), 2.36 (br, 1H, NH—CH$_2$), 3.22 (brs, 2H, CH$_2$), 5.77 (s, 1H, OH), 6.44-6.46 (dd, 1H, Arom-H), 6.92-6.93 (dd, 1H, Arom-H) 7.06-7.09 (t, 1H, Arom-H), 7.21-7.22 (t, 1H, Arom-H), 9.40 (br, s, 1H, NH), 9.74 (br, s, 1H, NH).

$^1$H NMR of GLP-112: DMSO-$d_6$, δ 1.56-1.58 (br, d, 3H, 3CH), 1.65-1.67 (br, d, 3H, 3CH), 1.90 (brs, 6H, 3CH$_2$), 2.12 (br, 1H, 3CH), 3.99 (br, 2H, CH$_2$), 6.40-6.443 (dt, 1H, Arom-H), 7.70-7.72 (dt, 1H, Arom-H), 9.11 (br, s, 1H, NH), 11.37 (s, 1H, NH).

$^1$H NMR of GLP-117: DMSO-$d_6$, δ 1.59-1.80 (br, m, 12H, 6CH$_2$), 2.01 (br, s, 3H, 3CH), 3.31 (br, s, 2H, CH$_2$), 4.63 (br, s, 1H, NH), 7.47-7.48 (d, 1H, Arom-H), 8.15-8.20 (dd, 1H, Arom-H) 8.67-8.68 (d, 1H, Arom-H), 11.08 (s, 1H, NH).

$^1$H NMR of GLP-118: DMSO-$d_6$, δ 1.58-1.69 (m, 3H, 3CH$_2$), 1.89 (br, s, 6H, 3 CH$_2$), 2.01 (s, 3H, 3CH), 4.01-4.03 (t, 1H, NH), 4.64 (br, s, 1H, CH$_2$), 7.66-7.68 (dd, 1H, Arom-H), 7.84-7.85 (d, 2H, Arom-H), 7.92-7.94 (dd, 1H, Arom-H) 9.04 (s, 1H, NH).

$^1$H NMR of GLP-119: DMSO-$d_6$, δ 1.53-1.62 (m, 12H, 6 CH$_2$), 2.01 (br, s, 3H, 3CH), 3.28 (br, s, 2H, CH$_2$), 3.39 (br, s, 1H, NH), 7.10-7.13 (m, 1H, Arom-H), 7.78-7.81 (m, 1H, Arom-H) 8.10-8.11 (d, 1H, Arom-H), 8.31-8.32 (m, 1H, Arom-H), 10.18 (s, 1H, NH—CO).

$^1$H NMR of GLP-120: DMSO-$d_6$, δ 1.55-1.64 (m, 12H, 6CH$_2$), 2.03 (br, s, 3H, 3CH), 2.13 (s, 6H, 2CH$_3$), 3.27 (br, s, 2H, CH$_2$), 3.38 (br, s, 1H, NH), 7.10 (s, 3H, Arom-H), 9.31 (s, 1H, NH—CO).

N.B. The identities of all compounds were confirmed with LC/MS and showed excellent purities (over 95%).

B. In Vitro Testing of DPP-IV Inhibitory Activity

Vildagliptin and the different tested compounds were dissolved in dimethyl sulphoxide (DMSO) and diluted with Tris buffer (pH 8.0, 50 mM) to achieve the required concentrations. DPP-IV inhibition assay was conducted using a kit purchased from Biovision (Milpitas, Calif., USA). Briefly, DPP-IV enzyme was diluted with Tris buffer and pipetted 50 µl into glass mini-cells. Subsequently the 25 µl of Tris buffer, vildagliptin or the tested compounds was added and incubated at 37° C. for 20 min protected from light. Finally a volume of 25 µl of DPP-IV substrate was added into each tube. The fluorescence generated from hydrolysis of the substrate was read at Ex/Em=360/460 nm using Modulus® single tube multimode reader (Promega, USA). Baseline fluorescence was recorded before incubation ($R_1$) and 20 min after incubation ($R_2$). Percentage inhibition was calculated according to the following equation:

$$\% \text{ inhibition} = (\Delta RFU \text{ test}/\Delta RFU\ E_C)*100$$

where, $\Delta RFU = R_2 - R_1$ and $E_C$ is the enzyme control (enzyme solution without inhibitor) which is considered 100% activity.

The standard DPP-IV inhibitor drug sitagliptin employed as positive control. Screening was done to all the synthesized compounds at 100 nM then a concentration-response study was conducted to the compounds that showed promising inhibitory effect to DPP-IV activity (>80% inhibition which was comparable to that of sitalgliptin). Sigmoidal concentration-response curves for DPP-IV % inhibition versus log concentration were plotted using Graphpad prism software, version 5.00 (GraphPad Software, Inc. La Jolla, Calif., USA). The $IC_{50}$ value corresponds to the concentration of sample needed to inhibit DPP-IV by 50%.

C. In Vivo Testing of DPP-IV Inhibitory Activity

Animals

The Biochemical and Research Ethical Committee of King Abulaziz University (Jeddah, Saudi Arabia), in accordance with the NIH guidelines, approved all procedures, and the animals received human care during the experimental period. Experiments were carried out using adult male Swiss albino mice (SWR), of 8-9 weeks age and 30-35 g weight. Animals were purchased from the animal house of the King Fahed Medical Research center (KFMRC), Jeddah, Saudi Arabia. Mice were kept at a constant temperature of 24-25° C. and were subjected to a controlled 12 h light-dark cycle; they had free access to water and pelleted diet ad libitum.

Induction of Diabetes

Nicotinamide (210 mg/kg b.w.), dissolved in saline, was injected intraperitoneally 15 min before the intraperitoneal injection of Streptozotocin (STZ) (Sigma, 180 mg/kg b.w.), which was freshly prepared in citrate buffer (pH 4.5). Control animals received both vehicles. During the experimental period, animals' food intake and body weight gain were monitored once a week. Twenty one days later, blood glucose levels of animals were determined and mice with fasting blood glucose over 130 mg/dL were considered diabetic.

Oral Glucose Tolerance Test

OGTT after Single Dose:

Oral glucose tolerance tests were performed in 14 h overnight fasted diabetic mice that were pretreated with a single oral dose of the tested compounds. Each of the tested agents as well as vildagliptin was administered as a single dose of 50 mg/kg. The drugs were suspended in carboxymethyl cellulose (CMC)-Na (1% in distilled water) and the dosing volume was adjusted at 10 mL/kg body weight of the mouse. Then an oral glucose load was administered (2 g/kg) 2 h after drug treatment. Blood glucose levels were determined using the Accu-check Go® (Roche Diagnostics, Michigan, USA). Samples were collected just before drug administration (fasting blood glucose), then at 2 h after drug treatment (immediately before glucose loading). Then blood sample collection was continued at 20, 40, 60 and 120 min intervals after glucose loading. The Area Under the Curve (AUC) (0-120 min) of blood glucose levels was calculated using the trapezoidal method.

Animal Groups

Animals were distributed between three categories of groups. Each group is composed of six animals (n=6) of either sex as follows:

Category 1: One group of animals were 14 h overnight-fasted normoglycemic mice and vehicle-treated (1% CMC-Na) at a dose of 10 ml/kg.

Category 2: Another group of animals was overnight fasted diabetic mice received the vehicle (1% CMC-Na) at a dosing volume of 10 ml/kg and served as a negative control.

Category 3: Overnight fasted diabetic mice received vildagliptin at a dose of 50 mg/kg in 1% CMC (in a volume of 10 ml/kg) and served as positive control.

Category 4: Animals of these groups were overnight fasted diabetic mice received the tested compounds at a dose of 50 mg/kg in 1% CMC (volume of 10 ml/kg).

OGTT after Multiple Doses of the Tested Compounds:

On the same groups that received the single dose treatment, the tested compounds were given daily by oral gavage for six consecutive days. On day 6, the overnight fasted diabetic mice were pretreated with the $6^{th}$ oral dose of the tested compounds. Two hours later, an oral glucose was loaded (2 g/kg/10 ml b.w.). Blood glucose levels were determined using the Accu-check Go®. Samples were collected just before drug administration (Fasting Blood glucose), then 2 h after drug treatment and before glucose administration. Samples collection was continued at 20, 40, 60 and 120 min intervals after glucose loading. The AUC (0-120 min) of blood glucose levels was calculated by the trapezoidal method.

Results and Discussion

Although the compounds in this study were designed against a specific target (DPP-4), we performed both phenotypic and target screening assays for each compound. This is because the main objective of this research is the discovery of advanced leads based on a well-established scaffold. The rationale for running both assays was the frequent literature mismatch between the data from in vitro and in vivo assays that might lead to a wrong decision about compounds to pick for further pharmacological studies.

TABLE 2

Synthesized final compounds and their in

| Compound Code | $R^1$ | $R^2$ | X | % Inhibition @ 100 nM | SD[¥] | $IC_{50}$ |
|---|---|---|---|---|---|---|
| 1 | Ph | H | OH | 79.97 | 4.89 | 5.88 |
| 2 | o-MePh | H | OH | 86.82 | 1.38 | 10.13 |
| 3 | p-MePh | H | OH | 28.38 | 0.77 | N/A |
| 5 | o-MeOPh | H | OH | 93.48* | 5.47 | 94.12 |
| 14 | o-CF3Ph | H | OH | 84.81 | 15.18 | 41.27 |
| 15 | m-CF3Ph | H | OH | 97.81* | 4.63 | 115.69 |
| 16 | o-COOMePh | H | OH | 45.61 | 0.27 | N/A |

TABLE 2-continued

Synthesized final compounds and their in

| Compound Code | R¹ | R² | X | % Inhibition @ 100 nM | SD¥ | IC$_{50}$ |
|---|---|---|---|---|---|---|
| 17 | m-OHPh | H | OH | 44.44 | 6 | 212.03 |
| 19 | o-CNPh | H | OH | 99.06* | 5.78 | 267 |
| 26 | m-CNPh | H | OH | 83.09 | 0.31 | 0.58 |
| 27 | o-FPh | H | OH | 67.04* | 1.86 | N/A |
| 30 | m-MePH | H | OH | 70.92* | 1.94 | N/A |
| 31 | m-FPh | H | OH | 56.23 | 2.52 | 62.3 |
| 43 | p-ClPH | H | OH | 51.64 | 0.734 | 101.5 |
| 53 | Bn | H | OH | 86.82 | 1.38 | 7.41 |
| 54 | p-FBn | H | OH | 57.12 | 3.28 | 87.09 |
| 59 | Phenethyl | H | OH | 67.04* | 3.47 | N/A |
| 60 | p-OHPh | H | OH | 20.11* | 7.54 | N/A |
| 110 | m-CNPh | H | H | 65.51 | 14.36 | 3.02 |
| 111 | m-OHPh | H | H | 79.63 | 3.91 | 2.08 |
| 112 | p-ClPh | H | H | 61.82 | 1.32 | 7.41 |
| 117 | 4-Cl-2-pyridyl | H | H | 83.14 | 3.87 | 5.42 |
| 118 | p-CNPh | H | H | 81.14 | 3.71 | 6.25 |
| 119 | 2-pyrid | H | H | 57.95 | 6.22 | 1.58 |
| 120 | 2,6-diMePh | H | H | 62.84* | 3.24 | N/A |
| Vildagliptin | | | | 78.1 | 0.31 | 0.552 |

*Inhibition at 1000 nM.
N/A = not available.
¥SD = Standard Deviation.

Among the tested 37 new derivatives listed in Table 2, eleven compounds exhibited enzymatic inhibition at 10 nM or lower (hit rate 30%). Three of these compounds showed potency at the picomolar level, i.e. their potency is higher than or comparable to vildagliptin. The majority of compounds have an aromatic group in the S1 position in place of the pyrrolylnitrile S1 moeity. The aromatic derivatives showed mixed results in enzyme inhibition tests, but this could be broadly explained by certain variation in the structures. If we closely check the inhibition results, the compounds with the highest potency possessed electron-withdrawing substituents on the aromatic ring. In this trend, we observed sub-nanomolar to single digit nanomolar activities for compounds with an electron withdrawing group placed at the meta position of the benzene ring. For example, the 3-cyanophenyl 26 had an enzymatic inhibition value of less than 1 nM.

The compounds without an alcoholic OH on the adamantyl ring and/or in which the electron withdrawing group is in a position other than the meta showed a small decrease in activity, although they are still in the range under 10 nM. For example, the m-cyano analogue 110, a deoxy congener of 26, exhibited activity at 3 nM. Other compounds having the same level of activity (1-10 nM) possess deactivated benzene, confirming the suitability of this structural feature for good binding with DPP-4. Some of these compounds have the electron-withdrawing group at the ortho position, such as the 2-pyridyl analogue 119, which has an inhibitory activity of 1.6 nM. The presence of a small electron-withdrawing group in the para position of the aromatic ring resulted in high enzyme binding activities (under 10 nM). This category of compounds is represented by potent inhibitors 112 (4-chloro), 117 (4-chloropyridyl) and 118 (4-cyano). The meta substitution with electron withdrawing but bulky group such as CF$_3$ (15) did not show good activity.

An exception of electron deficient ring feature is the compound 1, a phenyl derivative without substituents, which had a potency of IC$_{50}$ 5.9. The most surprising deviation from the above mentioned electronic requirement are the ortho tolyl analogues 2 that exerted inhibition at 10.3 and 6.3 nM respectively. Its meta (30) and para methyl (3) congeners as well as the ortho, ortho dimethyl homologue (120) have much weaker enzyme inhibition activities.

The aromatic ring having ortho substituents were universally weaker enzyme inhibitors than those with meta substituents, followed by para substituents, except the scantily understood ortho methyl analogues 2 and 103. Regardless, the nature of the majority of ortho or para substituents showed that the activities were not promising for these derivatives. The nitrile functionality at the P1 position provided high affinity towards the enzyme regardless its position (compounds 26, 110 and 118). The ortho compound 19, a compound with OH at the adamantyl group at P2 position, was an exception to nitrile performance. This can be considered a structure-activity relationship (SAR) issue pertaining to cooperative binding of all parts of the molecule (P1 and P2). In this regard, the presence of an electron withdrawing group at the para position gave inconsistent SAR features. Some para chloro and para nitrile analogues such as the deoxy congeners 112, 117 and 118 exerted high DPP-4 inhibition while the equivalent hydroxyadamantyl derivatives (such as 43) were weak inhibitors at high concentration. The fluoro analogues (27, 31) and trifluromethyl (14 & 15) analogues were generally weak regardless their position. The presence of bulky groups on the ring generally weakened the enzyme inhibition activities (5 & 16) while the pyridyl ring (117 and 119) conferred the best functionality in enzyme inhibition activity. All pyridyl derivatives had potencies under 10 nM. Encouraged by the pyridyl profile, we tested the isosteric thiazolyl ring. Unfortunately, the two tested thiazolyl compounds (98) were not active at reasonable levels.

The phenolic derivatives varied in their enzyme inhibition activities as the meta analogue (17) and para (60) exhibited very weak activity. These two derivatives have another hydroxyl group on the S2 adamantyl ring. The deoxy meta analogue (111) exhibited much better performance in the same assay.

The lack of biological activity of the alkyl deoxy analogue 113 can be attributed to poor solubility (the analogue is highly lipophilic). This observation agrees with the SAR of vildagliptin as reported by Villhauer et al.

TABLE 3

Fasting blood glucose of diabetic mice, treated with the studied compounds (50 mg/kg) for 6 consecutive days

| | Blood glucose level (mg/dL) | | | | | |
|---|---|---|---|---|---|---|
| | Day 1 | Day 2 | Day 3 | Day 4 | Day 5 | Day 6 |
| Normal control | 80.93* ± 8.64 | 95.60* ± 3.14 | 118.60* ± 5.89 | 108.20* ± 5.29 | 115.60* ± 3.72 | 116.10* ± 28.6; |
| Diabetic control | 200.20 ± 14.52 | 200.00 ± 21.36 | 279.40* ± 23.50 | 257.20 ± 22.39 | 269.60 ± 29.17 | 198.90 ± 34.79 |

TABLE 3-continued

Fasting blood glucose of diabetic mice, treated with the studied compounds (50 mg/kg) for 6 consecutive days

| | Blood glucose level (mg/dL) | | | | | |
|---|---|---|---|---|---|---|
| | Day 1 | Day 2 | Day 3 | Day 4 | Day 5 | Day 6 |
| Vildagliptin | 205.20* ± 19.89 | 119.40* ± 12.27 | 169.20* ± 4.91 | 197.80 ± 13.27 | 244.60 ± 15.36 | 165.00 ± 27.09 |
| 15 | 167.20* ± 18.12 | 87.80* ± 3.65 | 177.60* ± 31.42 | 166.80* ± 26.17 | 175.80* ± 27.78 | 161.80 ± 18.23 |
| 16 | 174.00 ± 12.41 | 93.80* ± 8.04 | 158.40* ± 18.39 | 127.40* ± 14.52 | 171.00* ± 20.54 | 107.60* ± 11.07 |
| 110 | 165.00* ± 2.34 | 107.20* ± 9.40 | 83.00* ± 8.65 | 105.60* ± 8.75 | 111.80* ± 15.40 | 121.40 ± 17.65 |
| 111 | 171.00 ± 3.937 | 122.40* ± 19.34 | 74.80* ± 5.809 | 153.00* ± 26.74 | 141.20* ± 15.69 | 180.20 ± 29.36 |
| 112 | 159.20* ± 12.13 | 114.40* ± 13.97 | 84.40* ± 6.08 | 115.40* ± 15.75 | 132.40* ± 11.34 | 122.00* ± 11.37 |
| 118 | 151.00* ± 8.66 | 124.00* ± 20.48 | 117.80* ± 22.79 | 141.00* ± 23.70 | 140.50* ± 11.72 | 151.30* ± 17.21 |
| 119 | 149.60* ± 5.49 | 103.40* ± 8.00 | 104.80* ± 12.55 | 148.60* ± 17.47 | 107.60* ± 9.28 | 118.60* ± 8.25 |

*Significantly different from corresponding diabetic control group at p <0.05

TABLE 4

Area under the curve in OGTT after oral glucose loading in diabetic mice 2 h single dose of studied compounds given orally in a dose of 50 mg/kg each.

| | AUC (mg · dL$^{-1}$ · min) | | | |
|---|---|---|---|---|
| =Treatment | X | S. E. | Δ from control | % change from diabetic control | Relative potency to vildagliptin |
| Normal control | 21067* | 2537 | — | — | — |
| Diabetic control | 51065 | 2216 | — | — | — |
| Vildagliptin | 34131* | 2217 | 16934 | −33.16 | 1 |
| 15 | 31080* | 2194 | 19985 | −39.13 | 1.18 |
| 16 | 30886* | 2115 | 20179 | −39.51 | 1.19 |
| 110 | 32264* | 2135 | 18801 | 36.81 | 1.11 |
| 111 | 25330* | 2213 | 25735 | −50.39 | 1.52 |
| 112 | 31770* | 1367 | 19295 | −37.78 | 1.14 |
| 118 | 28484* | 1567 | 22581 | −44.22 | 1.33 |
| 119 | 27068* | 1975 | 23997 | −46.99 | 1.417 |

*Different from corresponding diabetic control group significantly at p < 0.05

TABLE 5

Area under the curve in OGTT after oral glucose loading in diabetic mice 2 h pretreated with the tested compounds when given orally in a dose of 50 mg/kg each, for 6 days.

| | AUC (mg · dL$^{-1}$ · min) | | | | |
|---|---|---|---|---|---|
| =Treatment | X | S.E. | Δ from diabetic control | % change from diabetic control | Relative potency to vildagliptin |
| Normal control | 27103* | 2143 | — | — | — |
| Diabetic control | 52655 | 2481 | — | — | — |
| Vildagliptin | 33608* | 2199 | 19047 | −36.19 | 1 |
| 15 | 38926* | 2165 | 13729 | −26.07 | 0.72 |
| 16 | 24472* | 2213 | 28183 | −52.53 | 1.45 |
| 110 | 36830* | 2245 | 15825 | −30.05 | 0.83 |
| 111 | 47494 | 3309 | 6161 | −9.820 | 0.27 |
| 112 | 43708* | 2123 | 8947 | −16.99 | 0.46 |
| 118 | 24086* | 2163 | 28569 | −54.25 | 1.50 |
| 119 | 40405* | 2865 | 12250 | −23.26 | 0.64 |

*Significantly different from the diabetic control group at P < 0.05.

Nonetheless, our synthetic approach resulted in production of compounds with unexpected high enzymatic inhibitory potencies. In addition, the controlled physico-chemical properties of the tested compounds indicated that they could have good pharmacokinetic properties. Based on results of the enzyme inhibition assays, in vivo screening was conducted. The oral glucose tolerance test (OGTT) was performed over six days on diabetic mice. The glucose level was monitored daily (Table 3). The results were analyzed for activities after a single dose (Table 4) and after the 6th dose of the drug (Table 5).

Inspection of in vivo activities revealed that results are not completely parallel with enzymatic inhibition activities (Table 6).

TABLE 6

Matching the in vitro and the in vivo assays results. Compounds with weak initial point potency or IC$_{50}$ > 100 nM were not tested.

| | IC50 (nM) | R.P. to Vildagliptin (Single Dose) | R.P. to Vildagliptin (6 Days) |
|---|---|---|---|
| GLP-001 | 5.88 | Increased B.G. | Increased B.G. |
| GLP-002 | 10.13 | 0.42 | 1.2 |
| GLP-005 | 94.12 | 0.66 | 0.26 |
| GLP-014 | 41.27 | 0.12 | Increased B.G. |
| GLP-015 | >100 | 1.18 | 0.72 |
| GLP-017 | >100 | 0.26 | 1.42 |
| GLP-019 | >100 | 0.23 | 0.87 |
| GLP-026 | 0.58 | 0.32 | 1.3 |
| GLP-031 | 62.3 | 0.37 | 0.85 |
| GLP-043 | >100 | 0.26 | 1.39 |
| GLP-054 | 87.09 | Increased B.G. | Increased B.G. |
| GLP-059 | N/A | 0.52 | 0.83 |
| GLP-060 | N/A | 0.67 | 0.67 |
| GLP-110 | 3.02 | 1.11 | 0.27 |
| GLP-111 | 2.08 | 1.52 | 0.46 |
| GLP-112 | 7.41 | 1.14 | 0.79 |
| GLP-118 | 6.25 | 1.33 | 0.64 |
| GLP-119 | 1.58 | 1.417 | 1.26 |
| Vildagliptin | 0.552 | 1 | 1 |

R.P = Relative Potency

The results showed that some compounds consistently showed a high level of potency both in vitro and in vivo, in particular compounds N-(3-cyanophenyl)-2-[(3-hydroxyadamantan-1-yl)amino]acetamide (GLP-26) and 2-[(adamantan-1-yl)amino]-N-(pyridin-2-yl)acetamide (GLP-119). This indicates that their antihyperglycemic activity was due to their inhibition of DPP-4.

REFERENCES

Villhauer, E. B.; Brinkman, J. A.; Naderi, G. B.; Burkey, B. F.; Dunning, B. E.; Prasad, K.; Mangold, B. L.; Russel, M. E.; Hughes, T. E. 1-[[(3-Hydroxy-1-adamantyl)amino] acetyl]-2-cyano-(S)-pyrrolidine: a potent, selective, and orally bioavailable dipeptidyl peptidase IV inhibitor with antihyperglycemic properties. J. Med. Chem. 2003, 46, 2774-2789.

While the invention has been described in terms of its several exemplary embodiments, those skilled in the art will recognize that the invention can be practiced with modification within the spirit and scope of the appended claims. Accordingly, the present invention should not be limited to the embodiments as described above, but should further include all modifications and equivalents thereof within the spirit and scope of the description provided herein.

We claim:

1. A compound of generic structure

Formula I where X is selected from the group consisting of OH, H, $CF_3$, $CHF_2$, $CH_2F$, CN, OR, NHR, NHCOR, and $NHSO_2R$, where $R=(CH_2)_nCH_3$, and n=0-2, or where R=cyclopropyl, cyclobutyl, oxetanyl, or oxolanyl;

Ar is a substituted phenyl group having one or more substituents;

and n ranges from 0 to 5, wherein the one or more substituents is CN.

2. A compound which has the chemical structure:

3. A compound which has the chemical structure:

* * * * *